US006350617B1

United States Patent
Hindsgaul et al.

(10) Patent No.: US 6,350,617 B1
(45) Date of Patent: *Feb. 26, 2002

(54) DEVICE FOR DELIVERY OF MULTIPLE LIQUID SAMPLE STREAMS TO A MASS SPECTROMETER

(76) Inventors: Ole Hindsgaul, 9330 81$^{st}$ Ave., Edmonton, Alberta (CA), T6C 0X3; David C. Schriemer, 380 Whitlock Way, Calgary, Alberta (CA), T1Y 2C7

( * ) Notice: Subject to any disclaimer, the term of this patent is extended or adjusted under 35 U.S.C. 154(b) by 0 days.

This patent is subject to a terminal disclaimer.

(21) Appl. No.: 09/275,810

(22) Filed: Mar. 25, 1999

Related U.S. Application Data

(63) Continuation-in-part of application No. 09/069,656, filed on Apr. 29, 1998.
(60) Provisional application No. 60/079,622, filed on Mar. 27, 1998.

(51) Int. Cl.$^7$ .......................... G01N 30/02; H01J 49/04; H01J 49/10
(52) U.S. Cl. ........................ 436/173; 250/285; 250/288; 422/68.1; 422/100; 436/161; 436/174; 436/177; 436/180; 436/183
(58) Field of Search .................................. 250/288, 285; 210/198.2; 422/68.1, 100; 436/161, 173, 174, 175, 177, 183, 180

(56) References Cited

U.S. PATENT DOCUMENTS

| 2,534,181 A | 12/1950 | Roberts |
| 3,802,782 A | 4/1974 | Natelson |
| 3,863,495 A | 2/1975 | Schulz et al. |

(List continued on next page.)

FOREIGN PATENT DOCUMENTS

| EP | 0 338 572 B1 | 10/1989 |
| EP | 0 410 341 A2 | 1/1991 |
| EP | 0 966 022 | 12/1999 |
| JP | 06201650 A | 7/1994 |
| WO | WO 95/25737 | 9/1995 |
| WO | WO 97 43301 | 11/1997 |
| WO | WO 98/56028 | 12/1998 |
| WO | WO 99/13492 | 3/1999 |
| WO | WO 99/65058 | 12/1999 |

OTHER PUBLICATIONS

Biasi et al., "High Throughput Liquid Chromatography/Mass Spectrometric Analyses Using a Novel Multiplexed Electrospray Interface", *Rapid Communications in Mass Spectrometry*, 13:1165–1168 (1999).

Kostiainen et al., "Effect of Multiple Sprayers on Dynamic Range and Flow Rate Limitations in Electrospray and Ionspray Mass Spectrometry", *Rapid Communications in Mass Spectrometry*, 8:549–558 (1994).

Ogorzalek et al., "Evidence of Charge Inversion in the Reaction of Singly Charged Anions with Multiply Charged Macroions", *The Journal of Physical Chemistry*, 95:6412–6415 (1991).

(List continued on next page.)

*Primary Examiner*—Arlen Soderquist
(74) *Attorney, Agent, or Firm*—Burns Doane Swecker & Mathis LLP

(57) ABSTRACT

An electrospray apparatus employing multiple electrospray needles mounted in a circular arrangement sequentially delivers multiple sample streams to a mass spectrometer for analysis. One electrospray device includes an electrospray chamber, a rotatable needle supporting plate, a plurality of electrospray needles mounted on the plate, and a charger for applying a charge to droplets delivered to the electrospray chamber by the needles. Another electrospray device includes an electrospray chamber, a plurality of electrospray needles arranged in a circular arrangement, a charger, and a rotatable member for delivering gas phase ions from one needle at a time to the mass spectrometer. The rotatable electrospray apparatus provides fast repetitive analysis of simultaneously operating chromatography columns or other sample streams with a single mass spectrometer.

6 Claims, 6 Drawing Sheets

U.S. PATENT DOCUMENTS

| | | | |
|---|---|---|---|
| 3,915,652 A | * | 10/1975 | Natelson |
| 3,997,298 A | | 12/1976 | McLafferty et al. |
| 4,004,150 A | | 1/1977 | Natelson |
| 4,051,731 A | | 10/1977 | Bohl et al. |
| 4,055,987 A | | 11/1977 | McFadden |
| 4,281,246 A | | 7/1981 | White et al. |
| 4,607,163 A | | 8/1986 | Mizuno |
| 4,667,100 A | | 5/1987 | Lagna |
| 4,794,088 A | | 12/1988 | Miyaki et al. |
| 4,840,074 A | | 6/1989 | Jessop |
| 4,842,701 A | | 6/1989 | Smith et al. |
| 5,015,845 A | | 5/1991 | Allen et al. |
| 5,122,670 A | | 6/1992 | Mylchreest et al. |
| 5,288,514 A | | 2/1994 | Ellman |
| 5,306,412 A | | 4/1994 | Whitehouse et al. |
| 5,382,793 A | | 1/1995 | Weinberger et al. |
| 5,393,975 A | | 2/1995 | Hail et al. |
| 5,449,902 A | | 9/1995 | Onishi et al. |
| 5,516,698 A | | 5/1996 | Begg et al. |
| 5,538,897 A | | 7/1996 | Yates, III et al. |
| 5,605,616 A | | 2/1997 | Zepp |
| 5,618,693 A | | 4/1997 | McKnight et al. |
| 5,644,130 A | | 7/1997 | Raatz |
| 5,668,370 A | | 9/1997 | Yano et al. |
| 5,756,994 A | | 5/1998 | Bajic |
| 5,770,860 A | | 6/1998 | Franzen |
| 5,825,026 A | | 10/1998 | Baykut |
| 5,872,010 A | * | 1/1999 | Karger et al. ............... 436/173 |
| 5,917,184 A | | 6/1999 | Carson et al. |
| 6,066,848 A | * | 5/2000 | Kassel et al. ............... 250/288 |
| 6,191,418 B1 | * | 2/2001 | Hindsgaul et al. .......... 250/288 |

OTHER PUBLICATIONS

Rulison et al., "Scale–Up of Electrospray Atomization Using Linear Arrays of Taylor Cones", *Rev. Sci. Instrum.*, 64(3):683–686 (1993).

Shia et al., "JMS Letters", *Journal of Mass Spectrometry*, 32:247–250 (1997).

Zeng et al., "New Developments in Automated PrepLCMS Extends The Robustness and Utility of the Method for Compound Library Analysis and Purification", *Combinatorial Chemistry & High Throughput Screening*, 1:101–111 (1998).

Zeng et al., "Automated Analytical/Preparative High–Performance Liquid Chromatography–Mass Spectrometry System for the Rapid Characterization and Purification of Compound Libraries", *Journal of Chromatography A*, 794:3–13 (1998).

Printed materials from http://www.micromass.co.uk; Micromass Homepage and assorted pages.

Printed materials from http://www.micromass.co.uk; Press Centre, Pittcon 1999 Press Releases.

G. Hegy et al., "High throughput electrospray mass spectrometry of combinatorial chemistry racks with automated contamination surveillance and results reporting", Rapid Communications in Mass Spectrometry Chemical Abstracts, abstract No. XPOO2106591, vol. 126, No. 16, Apr. 21, 1997.

Qifeng Xue, et al., "Multichannel Microchip Electrosrapy Mass Spectrometry." *Analytical Chemistry*, vol. 69, No. 3, (Feb. 1997): pp. 426–430.

Simon Gaskell, "Electrospray: Principles and Practice." *Journal of Mass Spectrometry*, vol. 32, (1997): pp. 677–688.

Ken–Ichi Kasai, et al., "Frontal Affinity Chromatography: Theory For Its Application To Studies On Specific Interactions Of Biomolecules." *Journal of Chromatogaphy*, vol. 376 (1986): pp. 33–47.

Yen–Ho Chu, et al., "Affinity Capillary Electrophoresis—Mass Spectrometry For Screening Combinatorial Libraries." *Journal of American Chemical Society*, vol. 118, No. 33 (1996): pp. 7827–7835.

David S. Hage, et al., "Recent Advances In Chromatographic And Electrophoretic Methods For The Study Of Drug–protein Interactions." *Journal of Chromatography B*, vol. 699 (1997): pp. 499–525.

Kit S. Lam, "Application Of Combinatorial Library Methods In Cancer Research And Drug Discovery." *Oxford University Press*, vol. 12 (1997): pp. 145–167.

Jürgen Hille, "Enrichment And Mass Spectrometric Analysis Of Trace Impurity Concentrations In Gases." *Journal of Chromatography*, vol. 502 (1990): pp. 256–274.

Richard B. van Breemen, "Pulsed Ultrafiltration Mass Spectrometry: A New Method For Screening Combinatorial Libraries." *Analytical Chemistry*, vol. 69, No. 11 (Jun. 1997): pp. 2159–2164.

Ray Wieboldt, et al., "Immunoaffinity Ultrafiltration With Ion Spray HPLC/MS For Screening Small–Molecule Libraries." *Analytical Chemistry*, vol. 69, No. 9 (May 1997): pp. 1683–1691.

Michael L. Nedved, et al., "Characterization Of Benzodiazepine "Combinatorial" Chemical Libraries By On–Line Immunoaffinity Extraction, Coupled Column HPLC–Ion Spray Mass Spectrometry–Tandem Mass Spectrometry." *Analytical Chemistry*, vol. 68, No. 23 (Dec. 1996): pp. 4228–4236.

Shan Lin, et al., "Applications Of Frontal Affinity Chromatography To The Study Of Interactions Between Metal Ions And A Complex Biomaterial." *Analytical Chemistry*, vol. 68, No. 23 (Dec. 1996): pp. 4087–4093.

* cited by examiner

Expansion of Time Scale

DEVICE FOR DELIVERY OF MULTIPLE LIQUID SAMPLE STREAMS TO A MASS SPECTROMETER

This application is a continuation-in-part of U.S. Ser. No. 09/069,656, filed Apr. 29, 1998, which application claims the benefit of U.S. Provisional Application No. 60/079,622, filed Mar. 27, 1998. Each of these applications are incorporated herein by reference in their entirety.

BACKGROUND OF THE INVENTION

1. Field of the Invention

The invention relates to liquid delivery devices, and more particularly, the invention relates to devices for delivery of multiple liquid sample streams to a mass spectrometer for analysis of compound libraries.

2. Brief Description of the Related Art

In recent years, a large number of combinatorial chemistry techniques have been developed which permit vast libraries of diverse chemical compounds to be rapidly synthesized. In combinatory chemistry, a series of chemical reactions is conducted, typically employing a plurality of reagents at each step, to generate a library of compounds. Such techniques have the potential to greatly accelerate the discovery of new compounds having biologically useful properties by providing large collections of diverse chemical compounds for biological screening.

Mass spectrometry is emerging as an important tool for the interrogation of combinatorial libraries. To date, mass spectrometry has been used to assess library quality and, when coupled with molecular recognition technologies, has allowed for some success in the isolation and characterization of active library compounds. Applications of mass spectrometry have become increasingly important in combinatory chemistry and biological research.

Mass spectrometry obtains molecular weight and structural information on chemical compounds by ionizing the molecules and measuring either their time-off-light or the response of the molecular trajectories to electric and/or magnetic fields. The electrospray process is one of the most promising techniques for producing gas phase molecular ions for a wide range of molecular entities.

Mass spectrometry is also being increasingly relied on for the analysis of large numbers of samples. In particular, biomolecule sequencing (proteins, DNA) as well as the emerging field of proteomics require the mass spectral profiling of a large number of chromatographic fractions. For example, a two-dimensional electrophoretic separation such as SDS-PAGE (sodium docecyl sulfatepolyacrylamide gel electrophoresis) can lead to the separation of several thousand proteins from a cell extract, where each fraction requires mass spectral characterization.

According to a conventional electrospray process, a sample solution containing molecules of interest and a suitable solvent is pumped or drawn through an electrospray needle into an electrospray chamber. A potential of up to several kilovolts may be applied to the needle to generate a fine spray of charged droplets. Conversely, the needle may be held at ground and the solution sprayed into an externally generated electric field. The droplets are typically sprayed into the chamber at atmospheric pressure. Optionally, this chamber houses gas lines (e.g., $N_2$) to aid in the nebulization of the solvent stream and the disolvation or evaporation of solvent. The ions generated by the electrospray process are then guided into the mass spectrometer by appropriate electric field gradients. This typically requires multiple stages of pumping for the removal of excess neutrals, such as solvent vapor.

With this conventional electrospray apparatus, the electrospray needle is connected to a single sample stream and delivers the molecules contained therein by the electrospray process to the mass spectrometer for analysis. When multiple sample streams are prepared, it is time consuming to switch between successive sample streams. This is due to the fact that the available electrospray mass spectrometers are marketed with a single electrospray needle. Therefore, switching streams involves physically breaking the connection between the needle and one sample stream, and re-establishing a connection with the next stream. Aside from the time involved in switching streams, the possibility exists for cross-contamination of the various streams.

It would be desirable to permit multiple sample streams from multiple chromatography columns or from other sample sources to be easily connected to the electrospray apparatus of a mass spectrometer for intermittent analysis of the sample streams from multiple columns. It would also be desirable to automatically move from analysis of one sample stream to another to analyze a plurality of sample streams in as short a period of time as possible.

SUMMARY OF THE INVENTION

The present invention relates to electrospray devices employing multiple electrospray needles mounted to sequentially deliver multiple sample streams to a mass spectrometer for analysis.

In accordance with one aspect of the invention, an electrospray device for a mass spectrometer includes an electrospray chamber, a plurality of electrospray needles mounted on a support in a substantially circular arrangement, a rotatable member, and a charger. The electrospray needles are connectable to a plurality of sample streams for delivery of droplets of the sample streams to a mass spectrometer orifice. The rotatable member rotates to direct droplets of one of the sample streams at a time to the mass spectrometer orifice. The charger applies a charge to the droplets of the sample stream in the electrospray chamber and causes the droplets to be focused into a beam passing through the orifice into the mass spectrometer.

In accordance with another aspect of the present invention, a method is provided for delivering a plurality of sample streams to a mass spectrometer for analysis. The method includes the steps of: providing a plurality of sample streams to a plurality of electrospray needles mounted on a support; continuously spraying the sample streams with the electrospray needles; and sequentially providing an outlet of each of the electrospray needles at a delivery position for a predetermined dwell time by rotating and stopping a rotatable member to deliver the sample streams to the mass spectrometer.

BRIEF DESCRIPTION OF THE DRAWINGS

The invention will now be described in greater detail with reference to the preferred embodiments illustrated in the accompanying drawings, in which like elements bear like reference numerals, and wherein.

DETAILED DESCRIPTION OF THE PREFERRED EMBODIMENTS

A multiple needle electrospray apparatus for a mass spectrometer includes a plurality of electrospray needles 10 mounted on a rotatable plate 12 for sequential injection of multiple sample streams. The rotatable electrospray apparatus allows collection of data from multiple sample streams by a single mass spectrometer 20 in a short time by rotating the electrospray apparatus to sequentially monitor the stream from each of the needles 10 for a brief duration before rotating the plate 12 to another of the needles.

Examples of methods for screening compound libraries which involve analysis of multiple sample streams by electrospray mass spectrometry are described in U.S. patent application Ser. No. 09/070,131, filed on Apr. 29, 1998, and U.S. patent application Ser. No. 09/276,444, filed on even date herewith which are incorporated herein by reference in their entirety. According to one application of this method, a compound library is prepared, such as by combinatorial chemistry techniques. Multiple sample streams each of which contain a compound library or sublibrary are passed through a plurality of frontal chromatography columns. Each stream is passed through a single column to analyze the interaction of members of that sample stream with a target receptor within the column. The columns include a solid support or inert material on which the target receptor is bound or coupled. As the sample stream is continuously infused through the chromatography column, those compounds within the sample stream having a higher affinity for the target receptor (i.e., ligands) will be more strongly bound to the target receptors. When a compound has reached equilibrium with the column, it will break through and begin to pass out of the column with those compounds having the lowest affinity passing out of the column first. The sample streams exiting the chromatography columns are analyzed by electrospray mass spectrometry to determine the break through time for each compound. Mass spectrometry is particularly useful for this process because it allows for both detection and identification of the library members present in the sample streams exiting the columns.

Figure 1:
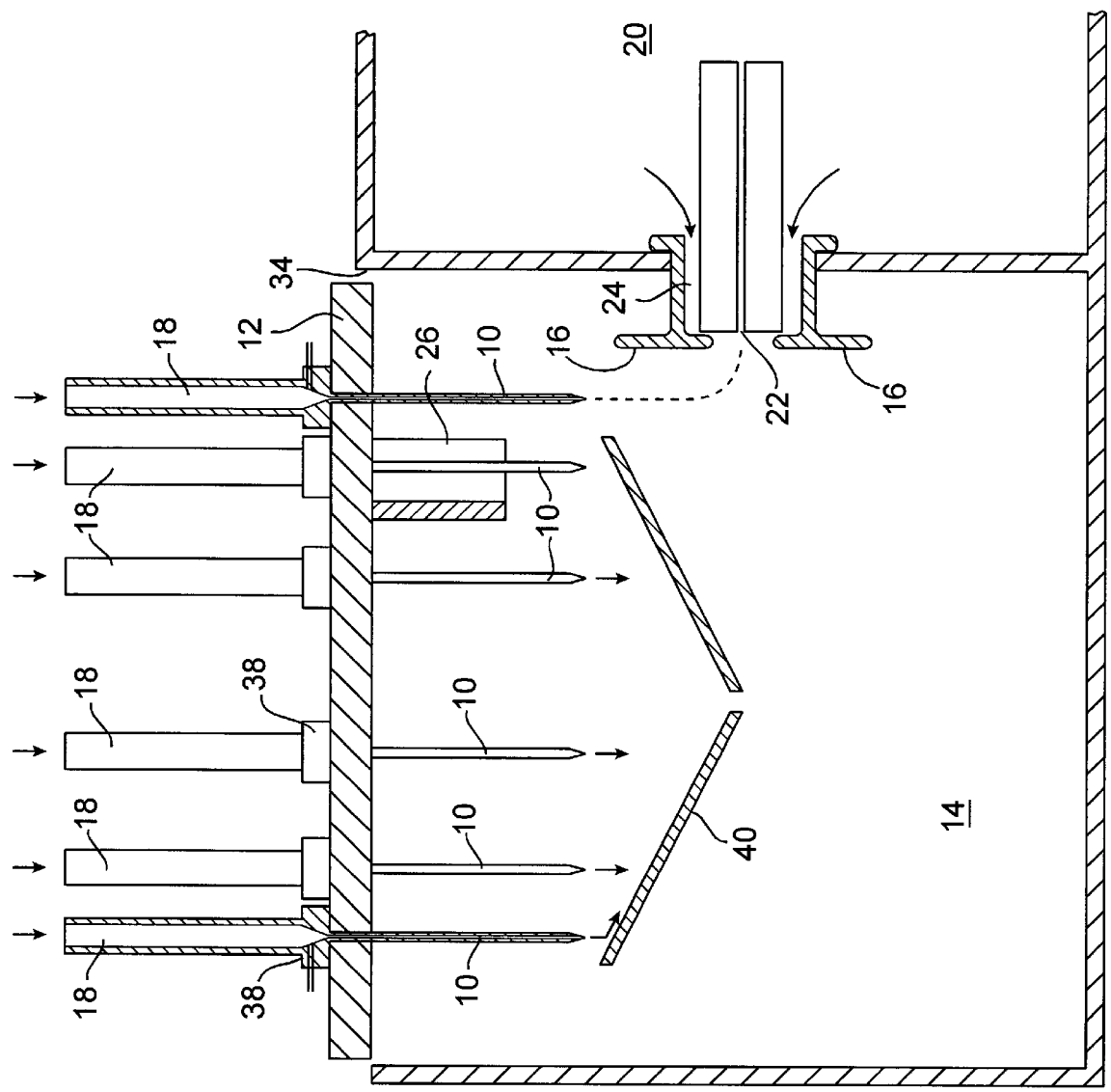
FIG. 1 is side view of a multiple needle electrospray apparatus for delivery of sample streams to a mass spectrometer.

FIG. 1 illustrates a first embodiment of an electrospray device for delivery of multiple liquid sample streams to the mass spectrometer 20. The electrospray device includes an electrospray chamber 14 for charging the droplets of a sample stream delivered by the electrospray needles 10 and delivering the charged ions in a beam to the mass spectrometer 20.

Figure 2:
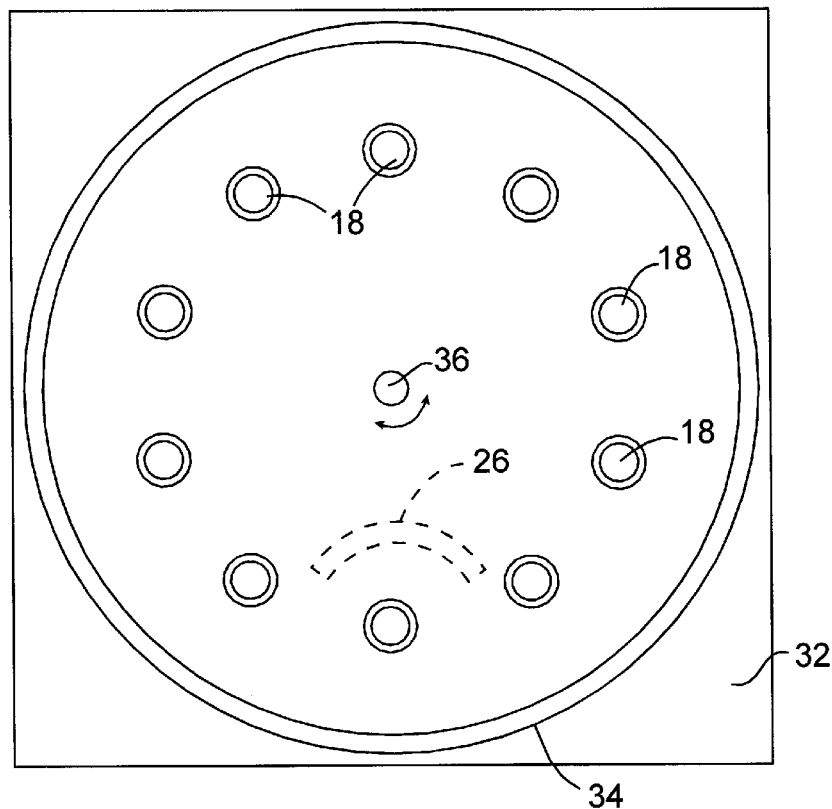
FIG. 2 is a top view of the multiple needle electrospray apparatus of FIG. 1.

The electrospray needles 10 each have an upper end mounted on the rotatable plate 12 in the circular arrangement illustrated in the top view of FIG. 2. The lower ends of the electrospray needles may be rotated into a reproducible delivery position within the electrospray chamber 14. The delivery position is at a precise location with respect to an orifice 22 of the mass spectrometer 20 which allows the sprayed droplets to be focused into a beam passing through the orifice. The delivery position is preferably within about ±0.5 mm of an ideal position. In fluid connection with each of the electrospray needles 10 is a sample source such as the chromatography columns 18 illustrated in FIG. 1. The chromatography columns 18 are preferably mounted on the top of the rotatable plate 12 or are connected to the needles 10 with flexible lines.

The electrospray chamber 14 surrounds the orifice 22 of the mass spectrometer and is open to atmospheric pressure. The electrospray chamber 14 surrounds the needles 10 for containment purposes. Only a needle 10 placed closest to a delivery position experiences a sufficiently high electric field and proximity for the efficient transmission of gas phase ions into the mass spectrometer 20.

The electrospray needles 10 are preferably coaxial needles which deliver the sample stream through an inner needle lumen and deliver a nebulizer gas, such as nitrogen, coaxially around the sample stream to break up the flow of the sample stream into a spray of droplets. Alternatively, the needles 10 may be single lumen needles delivering only the sample stream. The electrospray chamber 14 includes a charged sampling plate 16 surrounding the mass spectrometer entry orifice 22. The electrospray chamber 14 can also include an electrode 26 in the form of a half cylindrical portion of the front wall 28 of the electrospray chamber. The charged sampling plate 16 and the half cylindrical electrode 26 are charged with an electric potential preferably of about 0 to 6000 volts. The electric field established by the sampling plate 16 and the electrode 26 surrounds the grounded needle 10 and imparts a charge to the sprayed droplets.

According to an alternative embodiment of the invention, the charging of the sample stream droplets exiting the electrospray needle 10 may be accomplished by use of a charged electrospray needle, a biased sampling plate 16, and no electrode 26. The needle 10 may be continuously charged or may be charged only when the needle reaches the delivery position within the electrospray chamber 14 by an electrical contact.

A counter current drying gas, such as nitrogen, is delivered to the electrospray chamber 14 through a passageway 24 between the charged sampling plate 16 and the entry orifice 22 to assist in desolvating or evaporating the solvent from the sample stream to create fine droplets. According to an alternative embodiment of the invention, the drying gas may be delivered to the electrospray chamber 14 in manners other than through the passageway 24. In addition, the nebulizer gas may be delivered to the electrospray chamber 14 separately rather than by a co-axial flow through the electrospray needle. Both the nebulizer gas and the drying gas are introduced into the electrospray chamber 14 to obtain fine droplets of the sample stream. However, depending on the flow rate of the sample stream, the fine droplet size may be achieved without the need for a nebulizer gas and/or a drying gas.

The rotatable plate 12 is rotated by a motor connected to a drive shaft 36 of the plate. Preferably the motor is interfaced with a controller to control the rotation of the plate and the dwell times for each of the needles. Although the rotatable plate 12 has been illustrated as a circular plate, it should be understood that other plate shapes, such as multi-sided plates, rings, and the like, may be used without departing from the invention.

In operation, multiple sample streams are continuously delivered to each of the chromatography columns 18 from sample sources by, for example, a pump, such as a syringe pump. The sample streams exiting the columns 18 may be combined with a diluent in a mixing chamber or mixing tee 38 positioned between the column and the needle 10. The sample streams pass continuously through the electrospray needles 10 with a nebulizer gas delivered around the sample streams to break up the flow into droplets. Preferably, sample streams pass through all of the needles 10 simultaneously with only one of the streams from a needle positioned at the delivery position being analyzed by the mass spectrometer at a time. The sample streams from the remaining needles 10 are optionally collected by a tray 40 for delivery to waste.

To perform analysis of the multiple sample streams, one embodiment of the invention provides that the rotatable plate 12 is stepped in one direction, e.g., counter clockwise, through approximately half of the needles 10. When a quadrupole mass spectrometer is used a dwell time for each electrospray needle 10 ranges from about 0.5 to 10 seconds, preferably about 1 to 5 seconds before switching to the next column. After analysis of approximately half the sample streams, the rotatable plate 12 then returns clockwise to a home position and begins stepping in an opposite direction, e.g., clockwise, through the remaining half of the needles 10. Finally, the rotatable plate 12 returns again to the home position and repeats the procedure. The system operates continuously for a preset period of time related to the chromatographic requirements. Step times for rotation between successive needles is preferably less than about 100 msec, more preferably less than about 10 msec. The rotation of the plate 12 in one direction followed by reversing the rotation is preferred to prevent the feed lines for feeding the sample streams from the pump to the columns 18 from becoming twisted.

According to an alternative embodiment of the invention, the sample source, the pump or alternative, and the feed lines for delivery of the sample streams to the columns 18 may be mounted on the plate 12. With this embodiment, the plate 12 may be rotated continuously in one direction to sequentially analyze the flows from each of the needles without requiring the plate to reverse direction and return to a home position.

The mass spectrometer for use with the present invention may be any of the known mass spectrometers including a quadrupole mass spectrometer, quadrupole ion trap mass spectrometer, Penning or Paul ion trap mass spectrometer, FTICR (Fourier transform inductively coupled resonance) mass spectrometer, time-off-light mass spectrometer, and the like. A time-of-flight mass spectrometer is preferred due to its high spectral acquisition rate (>100 spectra per second). However, the slower quadrupole mass spectrometer may also be used which can record spectra at a rate of approximately 0.5 to 1 per second. The dwell times for analysis of each sample stream will vary depending on the spectral acquisition of the mass spectrometer used.

FIGS. 1 and 2 illustrate an electrospray device for analysis of sample streams from ten columns. When the electrospray device having ten columns is employed with a quadrupole mass spectrometer with analysis at a rate of about 1 spectrum per second and a dwell time of about 5 seconds per column is used, the system will take about 5 spectra from each column at a time and will cycle through all the columns in approximately 60 seconds.

Alternative embodiments of the invention may include different numbers of electrospray needles depending on the number of sample streams which are to be analyzed. The spacing of the multiple electrospray needles 10 is important to the operation of the electrospray device. In particular, the electrospray needles 10 should be spaced sufficiently to prevent cross over effects resulting from the sample stream from one columns influencing the analysis of the sample stream of an adjacent column. In addition, the electrospray needles 10 should be spaced as close together as possible to minimize the step times for rotation between adjacent needles. Preferably, the spacing between columns should be about 0.5 cm to 10 cm, depending on the mass spectrometer used. Alternatively, physical blocking members may be used to prevent cross over effects and allow closer needle placement.

Figure 3:
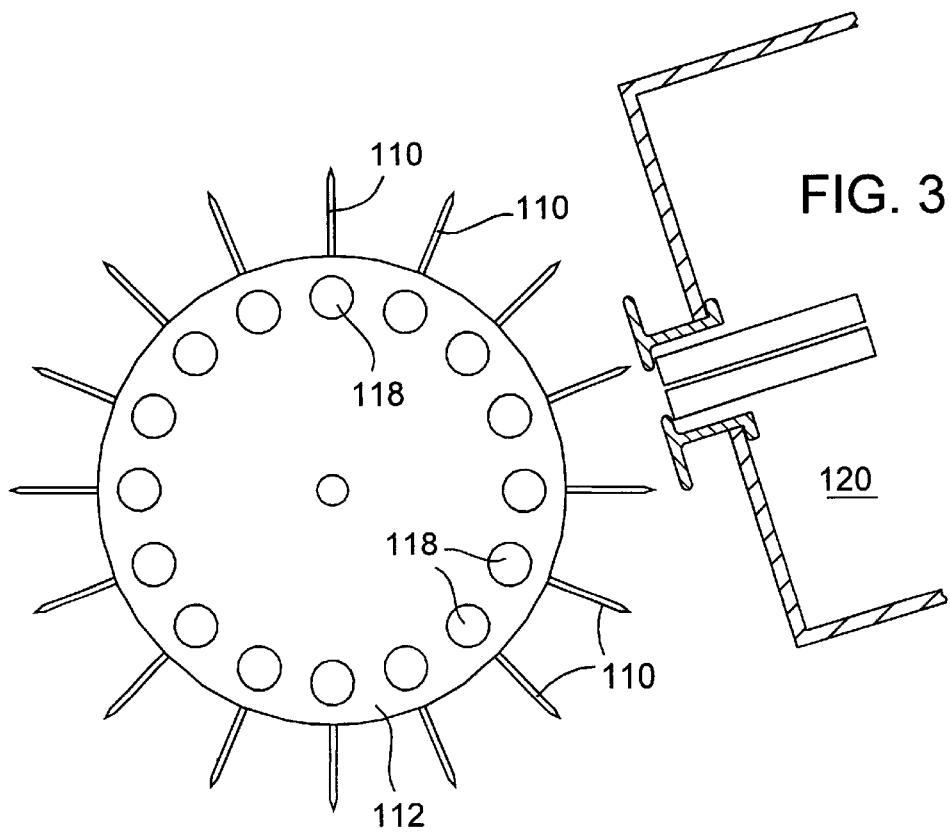
FIG. 3 is a schematic top view of an alternative embodiment of a multiple needle electrospray apparatus.

FIG. 3 is a top view of an alternative embodiment of a rotatable electrospray apparatus for delivery of sample streams to a mass spectrometer 120. The electrospray apparatus includes a plurality of electrospray needles 110 mounted in a radial arrangement on a rotatable plate 112. Each of the needles 110 are in fluid connection with a chromatography column 118. The radial arrangement of the electrospray needles 110 allows more columns 118 to be positioned on a rotatable plate 112 of a smaller diameter. According to this embodiment, the discharge ends of the needles 110 are preferably spaced a distance sufficient to prevent a cross over effect between adjacent needles. However, the columns 118 can be arranged close together around the periphery of the rotatable plate 112.

Figure 4:
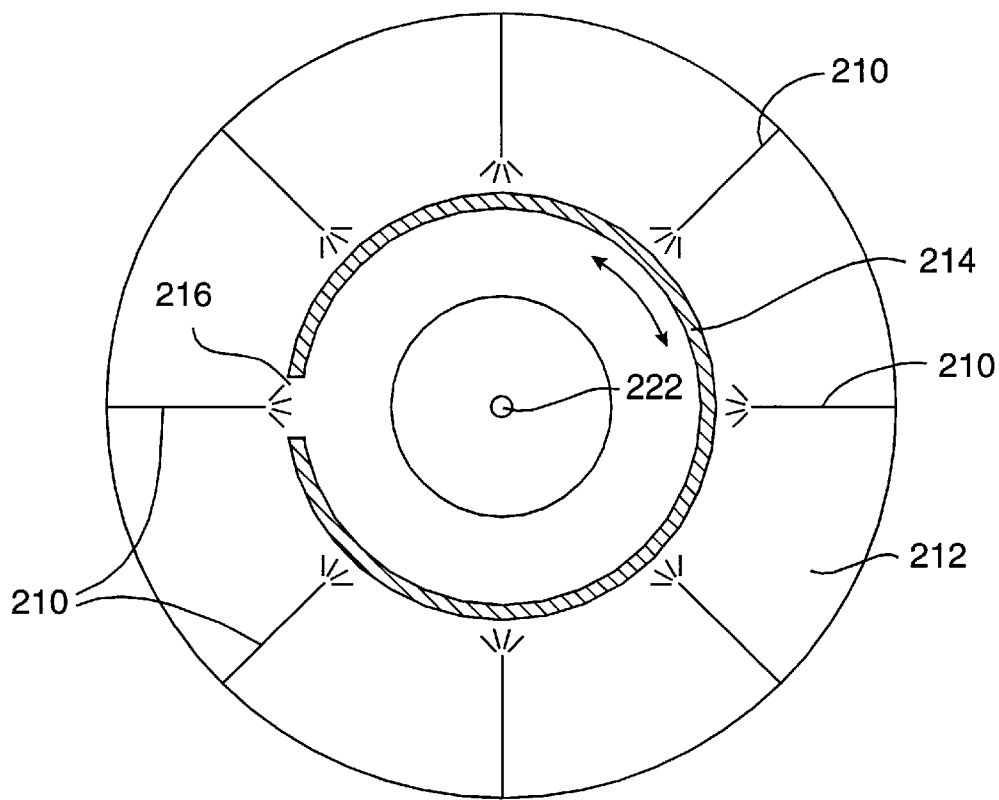
FIG. 4 is a schematic top view of an alternative embodiment of a multiple needle electrospray apparatus with non-rotating radially positioned needles.

FIG. 4 illustrates another embodiment of an electrospray device for delivery of multiple liquid sample streams to a single mass spectrometer. The electrospray apparatus of FIG. 4 includes a plurality of electrospray needles 210 mounted in a radially arrangement on a fixed plate 212 or other support structure. Each of the needles 210 are in fluid connection with a chromatography column or with another sample source. An inner rotatable blocking ring or cylinder 214 is positioned between the outlets of the needles 210 and a mass spectrometer entry orifice 222. The blocking member 214 is mounted on a drive shaft and rotated by a motor (not shown). The blocking member 214 includes a slot or opening 216 which allows the transmission of gas phase ions into the mass spectrometer. Optionally, the rotatable blocking member 214 may be a part of the ion optics for the mass spectrometer.

Figure 5:
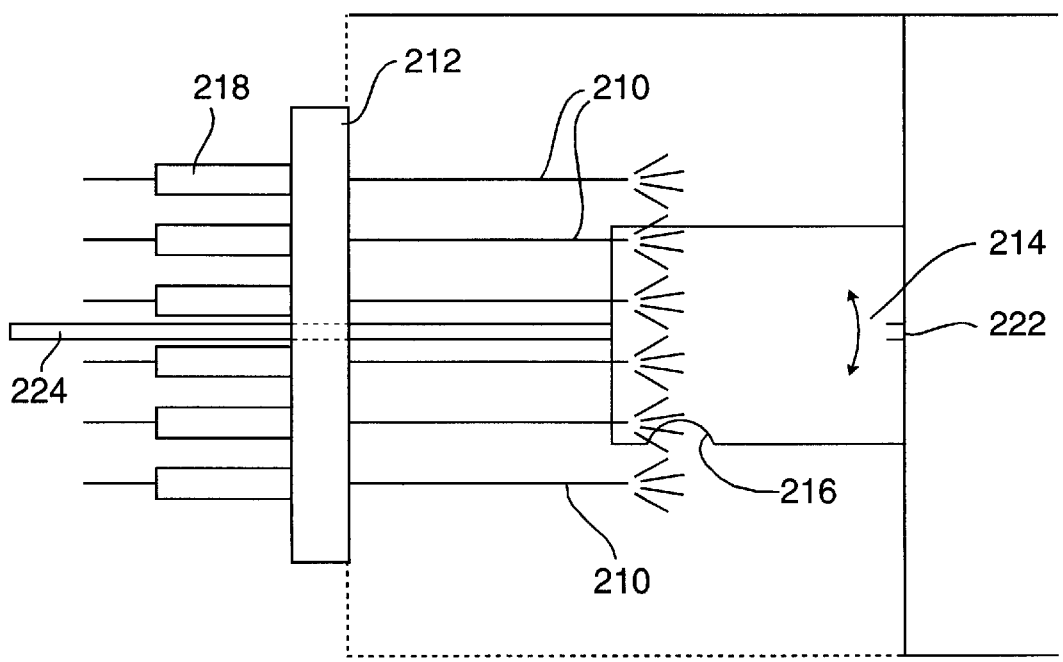
FIG. 5 is a schematic side view of an alternative embodiment of a multiple needle electrospray apparatus with parallel arranged non-rotating needles.

FIG. 5 illustrates a further alternative embodiment of a system for delivering multiple sample streams to a single mass spectrometer. The embodiment of FIG. 5 differs from that of FIG. 4 in that the needles 210 are arranged on the plate 212 in a circle, and the needles are substantially parallel to one another. As shown in FIG. 5, the chromatography columns 218 may be mounted on the fixed plate 212 or may be connected to the needles 210 by connecting lines. As illustrated in FIG. 5, the rotatable blocking member 214 is a cylindrical member which surrounds the mass spectrometer entry orifice 222 and includes an opening 216 which allows the transmission of gas phase ions from one of the needles at a time to the entry orifice. The rotatable cylinder 214 is rotated by a drive shaft 224 of a motor.

In the embodiments of FIGS. 4 and 5 the discharge ends of the needles 210 are preferably spaced by a distance which is sufficient to prevent a cross over effect between adjacent needles as described above. The blocking member 214 is stepped through the needle positions with dwell times for each needle varying depending on the mass spectrometer used as described above with respect to the embodiment of FIGS. 1 and 2. The advantages of the multiple needle electrospray devices of FIGS. 4 and 5 over the rotating needle versions of FIGS. 1–3 is that the sample stream feed lines are not rotated and twisted during operation.

The orientation and arrangement of the rotatable or non-rotatable support plate 12, 112, 212, the columns 18, 118, 218, and the electrospray needles 10, 110, 210 may be varied to achieve many different angular relationships for use with different types of mass spectrometers. For example, the rotatable plate may be positioned vertically and the columns and needles may be positioned horizontally. In addition, for some types of mass spectrometers the electrospray chamber is not enclosed by walls.

The present invention provides distinct advantages over prior art methods of operating and screening one column at a time. The rotatable electrospray apparatus allows multiple sample streams to be easily delivered to a single mass spectrometer and provides fast repetitive analysis of sample streams from simultaneously operating columns with a single mass spectrometer.

EXAMPLE

Figure 6:
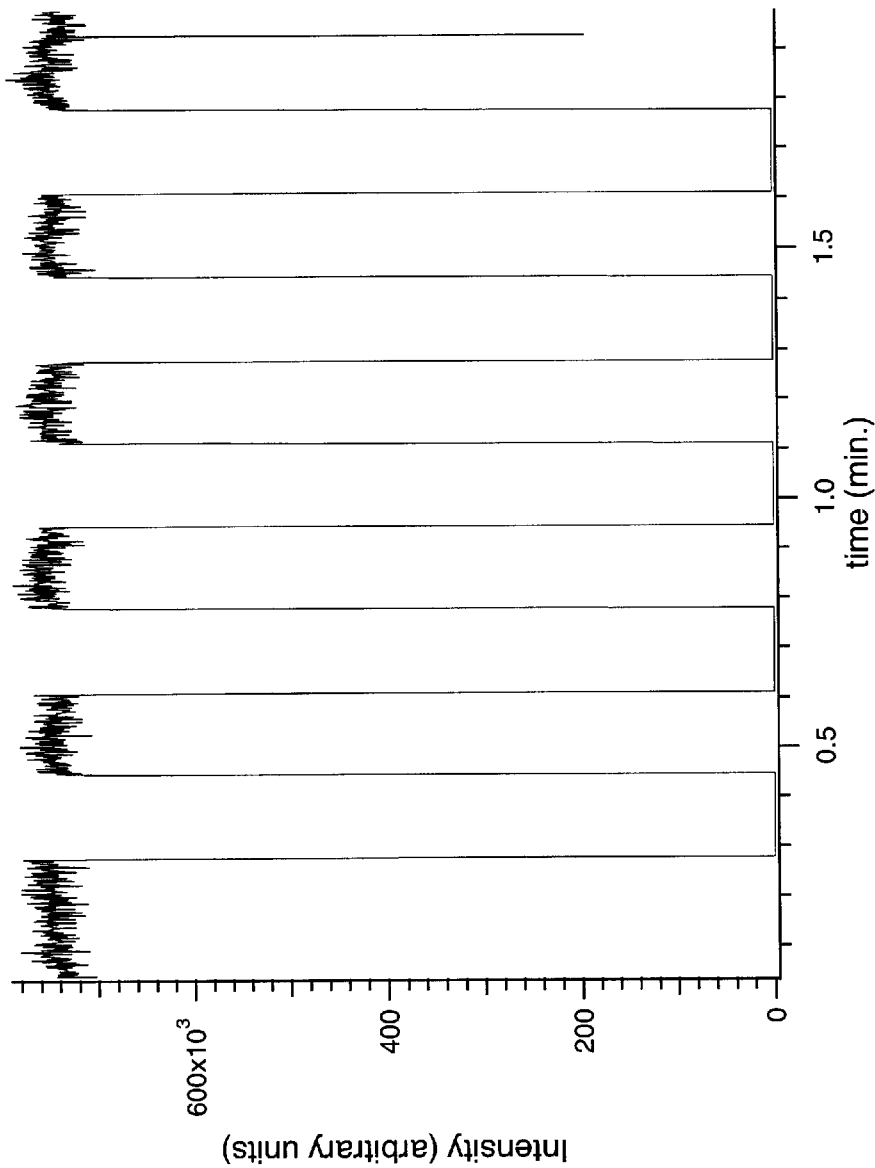
FIG. 6 is an ion chromatograph according to one example of the present invention.
Figure 7:
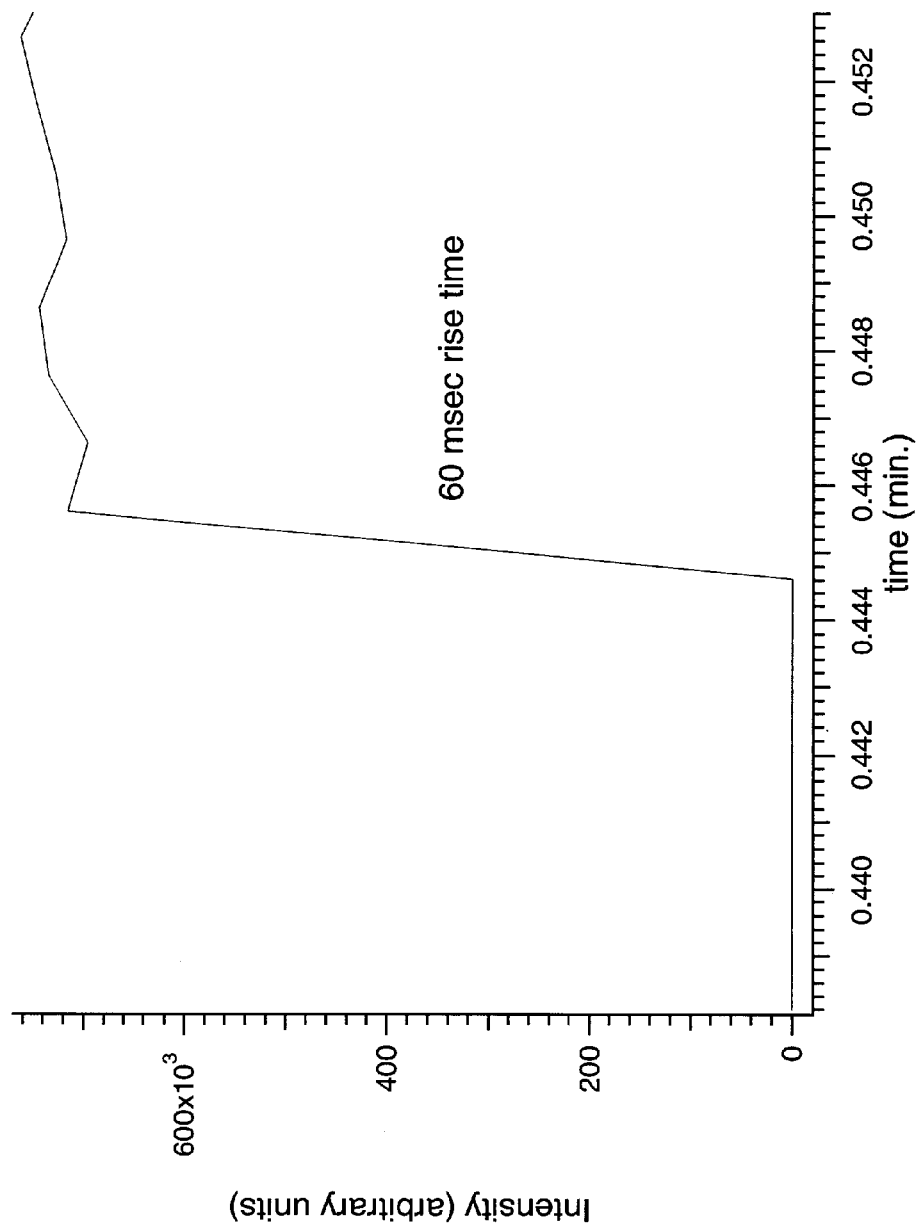
FIG. 7 is an enlarged view of a portion of the ion chromatograph of FIG. 6.

A four needle multisprayer apparatus was constructed according to the embodiment of FIG. 3, with a radial arrangement of needles on a rotatable plate or hub. The assembly was positioned vertically in front of the sampling plate as described herein. Four needles were positioned 90 degrees apart. As a demonstration of the device, a single needle was selected and connected to a flowing stream consisting of a 10 $\mu$M solution of a derivatized trisaccharide (with a m/z value of 681.2 u) in 1:1 acetonitrile:buffer (2 mM ammonium acetate, pH 7.2). No other streams were analyzed. A Hewlett-Packard series 1100 MSD electrospray mass spectrometer (quadrupole) was used, in selected ion monitoring mode. The needle connected to the flowing stream (10 $\mu$L/min) was positioned in front of the sampling orifice for maximum ion transmission, and mass spectrometer conditions were optimized for the monitoring of this compound. The needle assembly was then rotated 90 degrees at a fixed rate of 500 motor steps/sec, using a stepper motor capable of 200 steps/revolution, with dwell times of 10 seconds. This serves to swing the spraying needle out of its optimized position. At the end of 10 seconds, the spraying needle was swung back 90 degrees. FIG. 6 displays the ion chromatogram resulting from this experiment. As only one flowing stream was connected to the multisprayer, the signal is only observable when the stepper motor returns the flowing stream to its home position in front of the sampling orifice. Note that full signal is quickly and reproducibly established through five cycles. An expansion of the ion chromatogram of FIG. 6 is displayed in FIG. 7, demonstrating the fast rise time (<60 msec). This experiment was conducted at the maximum sampling rate of the quadrupole mass spectrometer.

Figure 8:
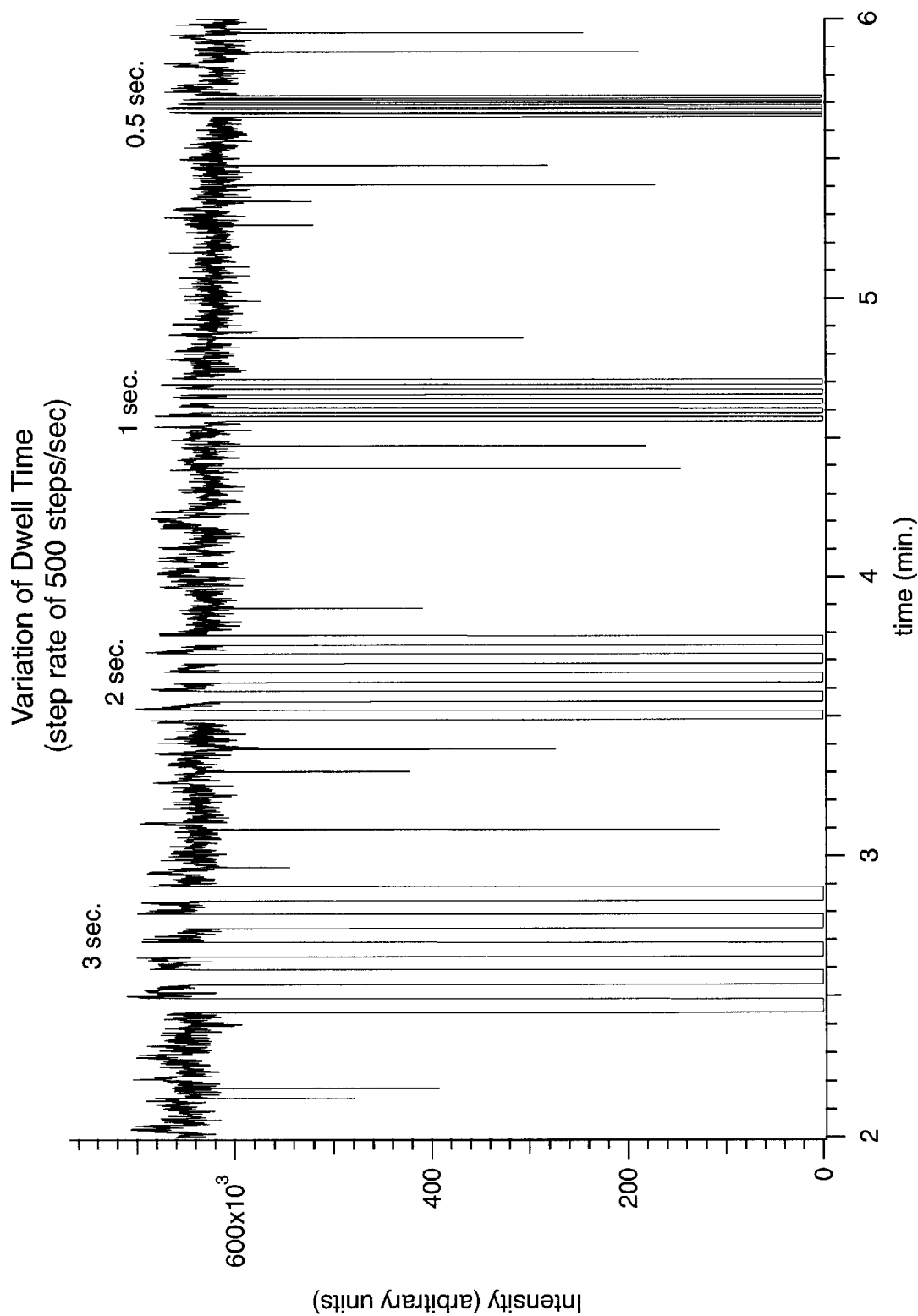
FIG. 8 is an ion chromatograph of a further experiment according to the present invention.

As a further demonstration, an experiment was conducted in which the step rate was fixed at 500 steps/sec and the dwell time in front of the sampling orifice varied from 3 to 0.5 seconds. The resulting ion chromatogram is shown in FIG. 8. In each case, the signal fully recovers, with rise times of <60 msec (note that the random peaks in the chromatogram reflect a general instability in the spray and is not a reflection of the multisprayer performance). FIG. 8 suggests that with the appropriately high sampling rate mass spectrometer (e.g., a TOF), shorter rise times and shorter dwell times should be achievable.

While the invention has been described in detail with reference to the preferred embodiments thereof, it will be apparent to one skilled in the art that various changes and modifications can be made and equivalents employed, without departing from the present invention.

What is claimed is:

1. An electrospray device for a mass spectrometer comprising:
    a plurality of electrospray needles mounted on a support in a substantially circular arrangement, the electrospray needles connectable to a plurality of sample streams for delivery of droplets of the sample streams to a mass spectrometer orifice;
    a rotatable member for directing droplets of one of the sample streams at a time to the mass spectrometer orifice;
    a charger for applying a charge to the droplets of the sample stream and causing ions to be focused into a beam passing through the mass spectrometer orifice; and
    a plurality of chromatography columns mounted on the support, wherein each of the chromatography columns is in fluid connection with one of the electrospray needles for delivery of the sample streams exiting the chromatography columns to the mass spectrometer.

2. An electrospray device for a mass spectrometer comprising:
    a plurality of electrospray needles mounted on a support in a substantially circular arrangement, the electrospray needles connectable to a plurality of sample streams for delivery of droplets of the sample streams to a mass spectrometer orifice;
    a rotatable member for directing droplets of one of the sample streams at a time to the mass spectrometer orifice;
    a charger for applying a charge to the droplets of the sample stream and causing ions to be focused into a beam passing through the mass spectrometer orifice; and
    a plurality of chromatography columns connected to the electrospray needles by fluid connection lines.

3. An electrospray device for a mass spectrometer comprising:
    a plurality of electrospray needles mounted on a support in a substantially circular arrangement, the electrospray needles connectable to a plurality of sample streams for delivery of droplets of the sample streams to a mass spectrometer orifice;
    a rotatable member for directing droplets of one of the sample streams at a time to the mass spectrometer orifice;
    a charger for applying a charge to the droplets of the sample stream and causing ions to be focused into a beam passing through the mass spectrometer orifice; and
    wherein the rotatable member is a rotatable cylindrical blocking member having an opening which allows droplets from one of the sample streams at a time to be delivered to the mass spectrometer and the rotatable cylindrical blocking member has an axis of rotation substantially aligned with the mass spectrometer orifice.

4. An electrospray device for a mass spectrometer comprising:
    a plurality of electrospray needles mounted on a support in a substantially circular arrangement, the electrospray needles connectable to a plurality of sample streams for delivery of droplets of the sample streams to a mass spectrometer orifice;

a rotatable member for directing droplets of one of the sample streams at a time to the mass spectrometer orifice;

a charger for applying a charge to the droplets of the sample stream and causing ions to be focused into a beam passing through the mass spectrometer orifice; and wherein the rotatable member is a rotatable blocking member having an opening which allows droplets from one of the sample streams at a time to be delivered to the mass spectrometer, the plurality of electrospray needles are mounted in fixed positions on the support and the rotatable blocking member is positioned between the plurality of electrospray needles.

5. A method of delivering a plurality of sample streams to a mass spectrometer for sequential analysis, the method comprising:

providing a plurality of sample streams to a plurality of electrospray needles mounted on a support plate;

continuously spraying the sample streams with the electrospray needles; and sequentially providing an outlet of each of the electrospray needles at a delivery position for a predetermined dwell time by maintaining the needles stationary and rotating and stopping a rotatable cylindrical blocking member with an opening to deliver the sample streams to the mass spectrometer.

6. A method of delivering a plurality of sample streams to a mass spectrometer for sequential analysis, the method comprising:

providing a plurality of sample streams to a plurality of electrospray needles mounted on a support plate;

continuously spraying the sample streams with the electrospray needles; and sequentially providing an outlet of each of the electrospray needles at a delivery position for a predetermined dwell time by maintaining the needles stationary and rotating and stopping a rotatable blocking member with an opening to deliver the sample streams to the mass spectrometer, wherein the rotatable blocking member is positioned between the electrospray needles.

* * * * *